United States Patent
Henderson

(10) Patent No.: US 9,770,523 B2
(45) Date of Patent: Sep. 26, 2017

(54) DECONTAMINATION METHODS

(71) Applicant: Integrated Solutions for Systems, Inc., Huntsville, AL (US)

(72) Inventor: Robert D. Henderson, Madison, AL (US)

(73) Assignee: Integrated Solutions for Systems, Inc., Huntsville, AL (US)

( * ) Notice: Subject to any disclaimer, the term of this patent is extended or adjusted under 35 U.S.C. 154(b) by 0 days.

(21) Appl. No.: 15/227,647

(22) Filed: Aug. 3, 2016

(65) Prior Publication Data

US 2017/0101078 A1    Apr. 13, 2017

Related U.S. Application Data

(62) Division of application No. 14/877,511, filed on Oct. 7, 2015.

(51) Int. Cl.
| | |
|---|---|
| *A61L 2/24* | (2006.01) |
| *A61L 2/18* | (2006.01) |
| *B60S 3/04* | (2006.01) |
| *A61L 2/22* | (2006.01) |

(52) U.S. Cl.
CPC .... *A61L 2/24* (2013.01); *A61L 2/18* (2013.01); *A61L 2/22* (2013.01); *B60S 3/04* (2013.01); *A61L 2202/122* (2013.01); *A61L 2202/14* (2013.01); *A61L 2202/15* (2013.01); *A61L 2202/17* (2013.01)

(58) Field of Classification Search
CPC ...... B60S 3/04; A61L 2/22; A61L 2/24; A61L 2/18
See application file for complete search history.

(56) References Cited

U.S. PATENT DOCUMENTS

| | | | |
|---|---|---|---|
| 3,261,659 A | 7/1966 | Schwichtenberg et al. | |
| 3,353,546 A | 11/1967 | Mahoney | |
| 4,461,097 A | 7/1984 | Thornton | |
| 5,076,304 A * | 12/1991 | Mathews | F16L 27/093 134/123 |
| 6,021,792 A | 2/2000 | Petter et al. | |
| 6,277,207 B1 * | 8/2001 | Gauthier | B60S 3/002 134/123 |
| 6,283,135 B1 * | 9/2001 | Fratello | B60S 3/04 134/123 |
| 7,045,021 B2 * | 5/2006 | Ewing | B08B 3/00 134/113 |

(Continued)

FOREIGN PATENT DOCUMENTS

RU    2548298 C1 *    4/2015    ............. F41H 7/03

OTHER PUBLICATIONS

English translation of RU2548298C1, Apr. 20, 2015.*

*Primary Examiner* — Regina M Yoo
(74) *Attorney, Agent, or Firm* — Ann I. Dennen; Lanier Ford Shaver & Payne PC

(57) ABSTRACT

A decontamination method for decontaminating an object of the present disclosure has steps including initiating spray in a first direction through one or more nozzles of a spray arm rotationally coupled to a control box, where the control box is in a first position and rotationally coupled to a leg of a gantry that is movably coupled to a track and rotating the control box to a second position based on profile data of the object.

8 Claims, 14 Drawing Sheets

(56) References Cited

U.S. PATENT DOCUMENTS

| | | | |
|---|---|---|---|
| 7,138,087 B1* | 11/2006 | Malkin | A61B 1/123 |
| | | | 422/1 |
| 8,272,143 B1 | 9/2012 | Hedman | |
| 8,858,724 B2 | 10/2014 | Black, Jr. | |
| 2002/0083653 A1 | 7/2002 | Hilbert | |
| 2002/0124870 A1* | 9/2002 | Jones | B60S 3/04 |
| | | | 134/18 |
| 2002/0179125 A1* | 12/2002 | Klos | C11D 11/0041 |
| | | | 134/36 |
| 2004/0159342 A1* | 8/2004 | Ewing | B08B 3/00 |
| | | | 134/29 |
| 2005/0201910 A1 | 9/2005 | Shou et al. | |
| 2007/0084650 A1 | 4/2007 | Schwei et al. | |
| 2007/0231190 A1* | 10/2007 | Hyde | A61L 2/07 |
| | | | 422/3 |
| 2009/0217944 A1 | 9/2009 | Munera et al. | |
| 2013/0098399 A1 | 4/2013 | Zeile et al. | |

* cited by examiner

DECONTAMINATION METHODS

CROSS-REFERENCE TO RELATED APPLICATION

This application claims priority to and is a divisional of U.S. patent application Ser. No. 14/877,511 entitled *Decontamination Systems and Methods* and filed on Oct. 7, 2015, which is incorporated herein by reference in its entirety.

BACKGROUND

In use, vehicles often can get contaminated with hazardous substances. For example, when in use vehicles may come in contact with chemical, biological, and radiological substances that are dangerous to humans, animals, or the environment. It is often necessary to employ decontamination procedures to neutralize or remove contaminants from the contaminated vehicles.

As an example, vehicle decontamination is often used during the quarantine of farms infected with foreign animal diseases. The effective and rapid decontamination of vehicles and equipment prevents the spread of contaminants into unaffected areas, thus reducing the overall human, economic and logistic cost.

SUMMARY

A decontamination system for decontaminating an object of the present disclosure has a gantry movably coupled to a track, and the gantry is situated adjacent the object. The gantry has at least one control box rotationally coupled to a first leg and at least one spray arm comprising a nozzle for spraying fluid that is rotationally coupled to the control box. Additionally, the decontamination system has logic configured for initiating spraying through the one or more nozzles in a first direction when the control box is in a first position, the logic further configured to rotate the control box to a second position based on profile data of the object.

A decontamination method for decontaminating an object of the present disclosure comprises the steps of: (1) initiating spray in a first direction through one or more nozzles of a spray arm rotationally coupled to a control box, the control box in a first position and rotationally coupled to a leg of a gantry that is movably coupled to a track; and (2) rotating the control box to a second position based on profile data of the object.

BRIEF DESCRIPTION OF THE DRAWINGS

The present disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure describes systems and methods for decontaminating vehicles. A decontamination system in accordance with an embodiment of the present disclosure comprises a shelter that houses a track and gantry system. A vehicle that has been subjected to chemical, biological, or radiological substances is driven into the shelter between a pair of tracks and beneath a gantry that is movably coupled to the tracks. Two control boxes are rotationally coupled to either side of the gantry. Additionally, two spray arms are rotationally coupled to each control box.

Upon detection of a vehicle in the shelter, the gantry passes over the length of the tracks so that a laser scanner can detect and measure the full profile of the vehicle and its location within the tracks. The laser scanner transmits the collected data indicative of the vehicle profile to a central computing device. Upon receipt, the central computing device develops a spray plan that consists of a series of orchestrated instructions to be given in a time controlled sequence to the gantry and spray arms. Taken together, the instruction result in movements that cover every surface of the vehicle. In this regard, the central computing device transmits instructions to the control boxes and the spray arms that raise, lower, and direct nozzles on the spray arms toward the vehicle as the gantry passes over the vehicle.

A fluid delivery system supplies decontaminants and water to the gantry, which is sprayed on the affected vehicle as described above. The fluid delivery system comprises one or more tanks that hold decontaminants and/or water. During operation, a user of the decontaminant system selects one or more of the decontaminants and a concentration of the selected decontaminants to be delivered to the gantry via a handheld device. The handheld device communicates with the central computing device, which controls pumps in fluid communication with the tanks. Thus, the concentration of a selected decontaminant may be user-controlled.

Figure 1:
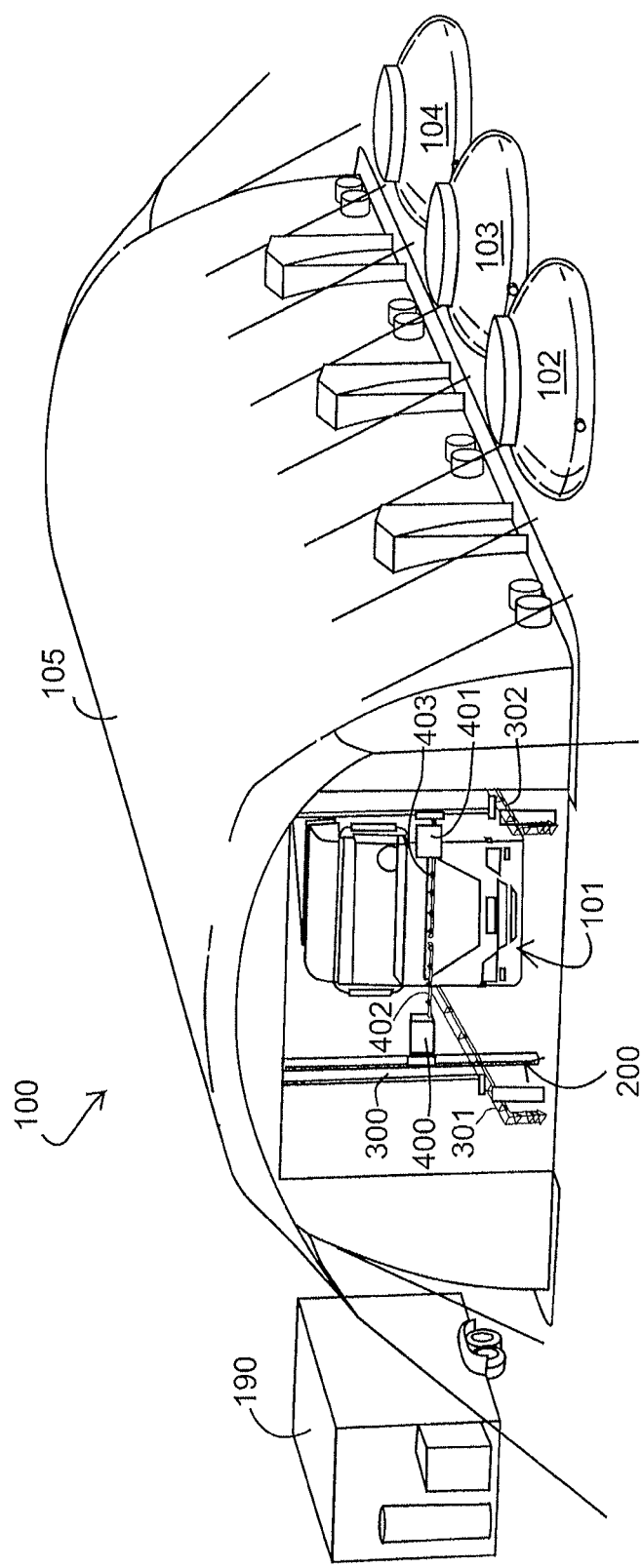
FIG. 1 is a perspective view of an exemplary decontamination system in accordance with an embodiment of the present disclosure.

FIG. 1 is a decontamination system 100 in accordance with an embodiment of the present disclosure. The decontamination system 100 comprises a shelter 105 and one or more tanks 102-104 that contain decontaminants and/or water.

Within the shelter 105 is a track and gantry system 200. Note that FIG. 1 depicts the track and gantry system 200 in a position wherein a gantry 300 is positioned closest to an opening 106 of the shelter 105. Further, spray arms 402 and 403 that are coupled to the gantry 300 via control boxes 400 and 401 are positioned in front of a vehicle 101 perpendicular to tracks 301 and 302.

The vehicle 101 enters one side of the shelter 105 and is positioned between the tracks 301 and 302 and beneath the gantry 300. Note that FIG. 1 shows the vehicle 101 in a position at the end of the track and gantry system 200 closest to the opening 106 of the shelter 105. This position of the vehicle 101 is hereinafter referred to as the "ready position."

Once the vehicle 101 is in the ready position, a driver (not shown) of the vehicle 101 exits the vehicle 101 and the shelter 105. When the driver has exited the shelter 105, decontamination of the vehicle 101 begins. The decontamination process is described further herein.

When decontamination is complete, the driver may then reenter the vehicle 101. The spray arms 402 and 403 are moved, and the driver can drive the vehicle 101 from the shelter 105 via the opening 106.

FIG. 1 further depicts a trailer 190. The trailer 190 comprises various components of the system, including the central computing device (not shown) and the fluid delivery system (not shown), both of which are described further herein. Note that in one embodiment of the present disclosure, all components of the decontamination system 100 may be broken down, stored, and/or transported in the trailer 190.

Further note that the present disclosure describes decontamination of a vehicle. However, other objects may be decontaminated by the decontamination system in other embodiments. For example, the decontamination system may be used to decontaminate farm equipment.

Figure 2:
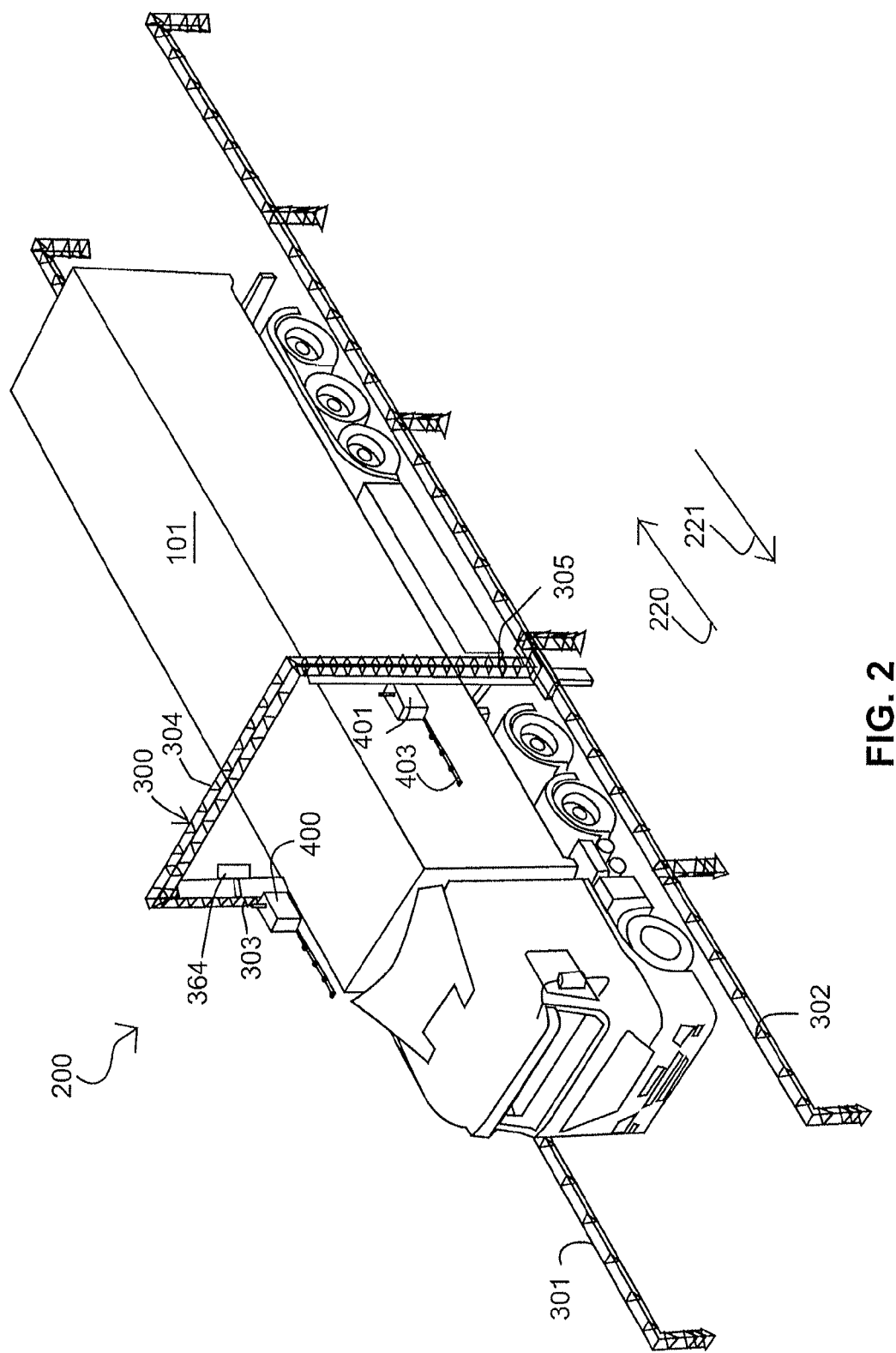
FIG. 2 is a perspective view of the decontamination system of FIG. 1 with the shelter removed.

FIG. 2 is a track and gantry system 200 in accordance with an embodiment of the present disclosure that comprises the parallel tracks 301, 302 and the U-shaped gantry 300. For clarity of discussion, the track and gantry system 200 is shown in FIG. 2 with the shelter 105 removed. Further, the vehicle 101 is positioned between the parallel tracks 301 and 302 and beneath the U-shaped gantry 300.

The inverted U-shaped gantry 300 comprises two vertical legs 303 and 305. Coupling together the top ends of the two vertical legs 303 and 305 is a horizontal bridge 304. Further, opposing ends of each leg 303 and 304 are movably coupled to respective tracks 301 and 302. During scanning, decontamination and/or rinsing, the U-shaped gantry 300 moves bi-directionally along the tracks 301 and 302, as indicated by reference arrows 221 and 220.

Coupled to the U-shaped gantry 300 is a laser scanner 364. As will be described in more detail herein, prior to decontamination, the gantry 300 moves along tracks 301 and 302 from the front of the vehicle 101 to the back of the vehicle 101. In one embodiment, proximity sensors (not shown) are used to detect the front and backend of the vehicle 101. As the gantry 300 moves, the laser scanner 364 collects data indicative of a profile of the vehicle 101. In one embodiment, the laser scanner 364 collects data indicative of x, y, and z coordinates of the profile of the vehicle.

Note that FIG. 2 depicts a position of the gantry 300 that is approximately midway down the length of the vehicle 101, and this position occurs as the vehicle is being scanned, decontaminated, or rinsed. The initial position of the track and gantry system 200 prior to beginning decontamination is described hereinabove with reference to FIG. 1.

Figure 3:
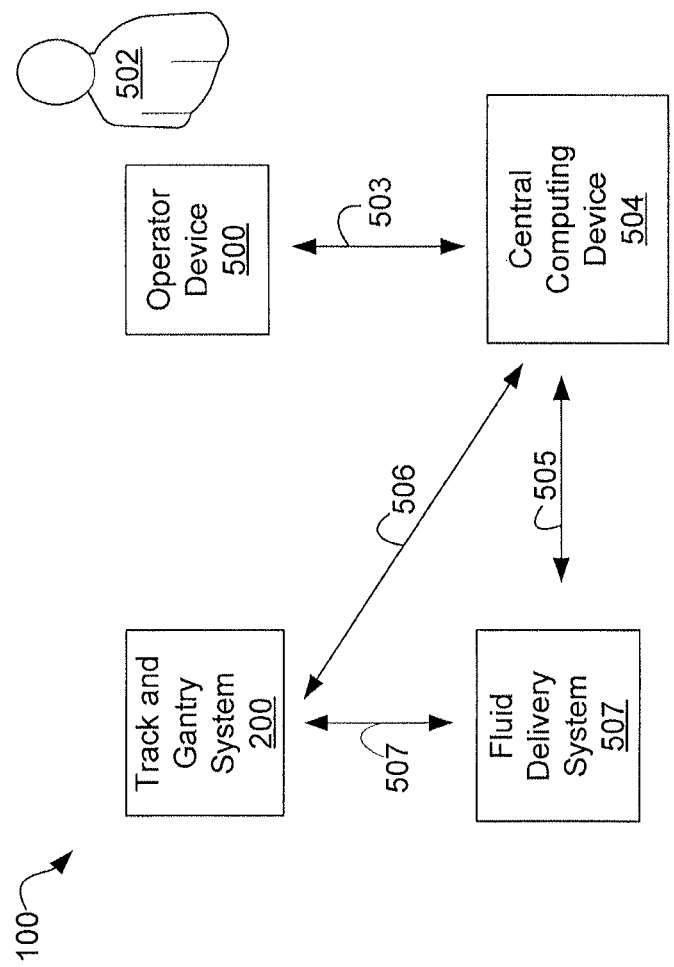
FIG. 3 is a block diagram of the decontamination system of FIG. 1.

FIG. 3 is a block diagram depicting the decontamination system 100 in accordance with an embodiment of the present disclosure. The decontamination system 100 comprises the track and gantry system 200, an operator device 500, a fluid delivery system 507, and a central computing device 504 (collectively referred to herein as system components).

The central computing device 504 is any type of computing device that can interface with the other system components either via cables or wirelessly. The central computing device 504 controls the system 100 at direction from an operator 502 via the operator device 500.

The central computing device 504 may be, but is not limited to, a server or a personal computer (PC). The central computing device 504 is communicatively coupled to the operator device 500 via a communication link 504, to the track and gantry system 200 via communication link 504 and to the fluid delivery system via communication link 505

In one embodiment, some or all communication links 503, 506, and 505 are effectuated with a wireless local area network (WLAN). In the embodiment, the central computing device 504 communicates bi-directionally with the operator device 500, the track and gantry system 200, and the fluid delivery system 507 via the WLAN.

In another embodiment, some or all communication links 503, 506, and 505 are established via direct cabling. For example, the link 506 between the central computing device 504 and the track and gantry system 200 and the link 505 between the central computing device 504 and the fluid delivery system 507 may be an Ethernet cable.

Note that communication between the system components, including the central computing device 504, the operator device 500, the track and gantry system 200, and the fluid delivery system 507, is described as being effectuated via a WLAN or Ethernet. However, other types of hardware and software may be used to establish the communication links between the system components in other embodiments. The present disclosure is not intended to limit the type of hardware and/or software that communicatively couples the system components.

The operator device 500 is any type of computing device that may be used by an operator 502 to control the system 100 via the central computing device 504, including, but not limited to, a tablet, e.g., an iPad™, a personal digital assistant (PDA), a cell phone, or a laptop computer. In operation, the operator 502 inputs data indicative of instructions for controlling the system 100. The data indicative of the instructions is sent to the central computing device 504, which controls the system 100 accordingly.

The fluid delivery system 507 comprises components for delivering decontaminants (not shown) and water (not shown) to the gantry 300. In turn, the gantry 300 sprays the vehicle 101 with the fluids delivered. Thus, the fluid delivery system 504 is in fluid communication with the track and gantry system 200 via piping 507. As will be described further with reference to FIG. 10, the fluid delivery system 507 comprises a plurality of conduits, pumps, flow meters, and tanks 102-104 (FIG. 1) for delivering the fluids to the gantry 300.

Figure 4:
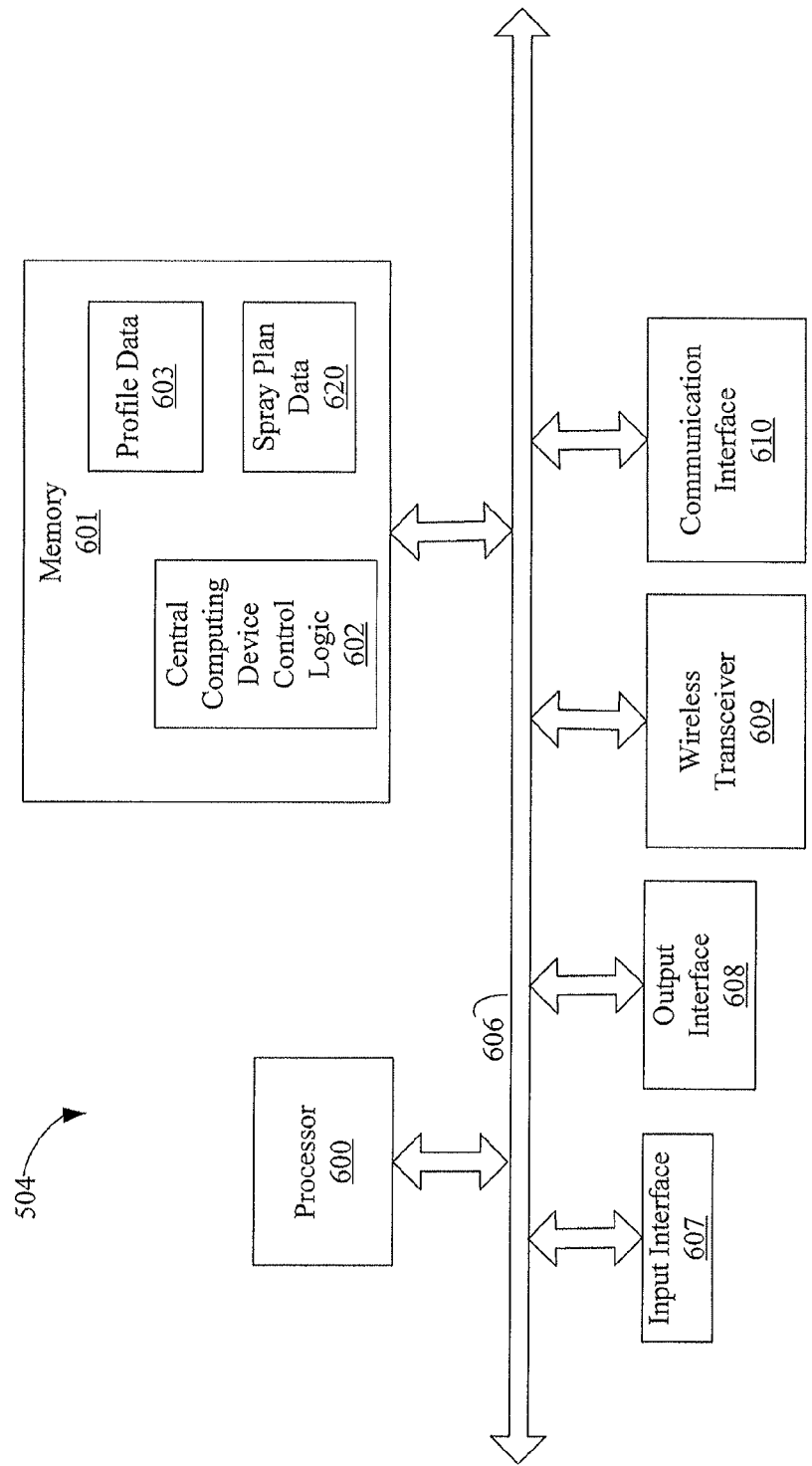
FIG. 4 is a block diagram of an exemplary computing device of the decontamination system of FIG. 3.

FIG. 4 is a block diagram of an exemplary central computing device 504 in accordance with an embodiment of the present disclosure. The exemplary computing device 504 comprises processor 600, output interface 608, input interface 607, a Wi-Fi transceiver 609, and a communication interface 610. Each of these components communicates over local interface 406, which can include one or more buses.

The central computing device 504 further comprises central computing device control logic 602. Central computing device control logic 602 can be software, hardware, or a combination thereof. In the exemplary central computing device 504 shown in FIG. 4, control logic 602 is software stored in memory 601. Memory 601 may be of any type of memory known in the art, including, but not limited to random access memory (RAM), read-only memory (ROM), flash memory, and the like.

As noted hereinabove, the central computing device control logic 602 is shown as stored in memory 601. When stored in memory 601, the central computing device control logic 602 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium Processor 600 may be a digital processor or other type of circuitry configured to run the central computing device control logic 602 by processing and executing the instructions of the central computing device control logic 602. Further, the processor 600 communicates with and drives the other elements within the central computing device 504 via the local interface 406.

The Wi-Fi transceiver 609 may be, for example, a low-powered radio device, e.g., a radio semiconductor, radio frequency antenna (RF antenna) or other type of communication device, which communicatively couples the central computing device 504 with the other system components, e.g., the operator device 500 (FIG. 3). In this embodiment, the Wi-Fi transceiver 609 is a wireless transceiver that is configured to transmit and receive messages wirelessly from the system components.

The output interface 608 is any type of device for providing information to the operator 502 (FIG. 3). In this regard, the output interface may be, for example, a backlit liquid crystal display (LCD) screen (not shown). Other types of output interfaces 608 may be, for example, an audio device that provides instructions to the operator 502 audibly, light emitting diodes (LED) that show status of the system 100, or any other type of output interface that provides sensory information to the operator. While some examples have been given, other types of output interfaces may be used in other embodiments of the present disclosure The input interface 607 is any device that enables the operator to input data into the central computing device 504. In one embodiment, the input interface 607 is a touchscreen that allows the operator 502 to provide information to the central computing device 504 by selecting areas on the touch screen. In another embodiment, the input interface may be, for example, a keyboard or a microphone. In this regard, the operator may use the keyboard to type data into the central computing device 504. While some examples have been given, other types of input interfaces may be used in other embodiments of the present disclosure.

The communication interface 610 is any other type of communication interface that the central computing device 504 may use to communicate with the system components and/or a network (not shown). As an example, the communication interface 610 may be an Ethernet interface that enables the central computing device 504 to communicate with the system components, e.g., the fluid delivery system 507. As another example, the communication 610 may be any type of device that allows the central computing device 504 to communicate with the Internet.

The central computing device 504 further comprises profile data 603. The profile data 603 is data indicative of a profile of a vehicle 101 (FIG. 2) that is being decontaminated. As indicated hereinabove with reference to FIG. 2, the track and gantry system 200 (FIG. 2) comprises a laser scanner 364 (FIG. 2) that scans the vehicle 101. The laser scanner 364 collects data indicative of the x, y, and z coordinates of the profile of the vehicle 101 to be decontaminated. The laser scanner 364 transmits the profile data indicative of the scan to the central computing device 504. Upon receipt, the central computing device control logic 602 stores the data received as the profile data 603.

Upon receipt or prior to beginning decontamination, the central computing device control logic 602 translates the profile data 603 into a spray plan for spraying the vehicle 101 and stores data indicative of the spray plan as spray plan data 620. In translation, the central computing device control logic 602 generates a three-dimensional mode of the vehicle 101 and generates the spray plan data 620 based upon the three-dimensional model. Note as described above, the profile data 603 comprises the x, y, and z coordinates of the profile of the vehicle 101. Thus, in translation, the central computing device control logic 602 analyzes the coordinates and determines instructions to be sent to the track and gantry system 200 for moving the components of the track and gantry system 200 so that the surfaces of the vehicle are sprayed with decontaminants and rinse. As a mere example, the coordinates may define a height of the vehicle 101 as ten (10) feet. Thus, the central computing device control logic 602 would translate this data into an instruction that moves the spray arms 402 and 403 from ground level and up the front of the vehicle 101 ten (10) feet. This process is described further herein.

Figure 5:
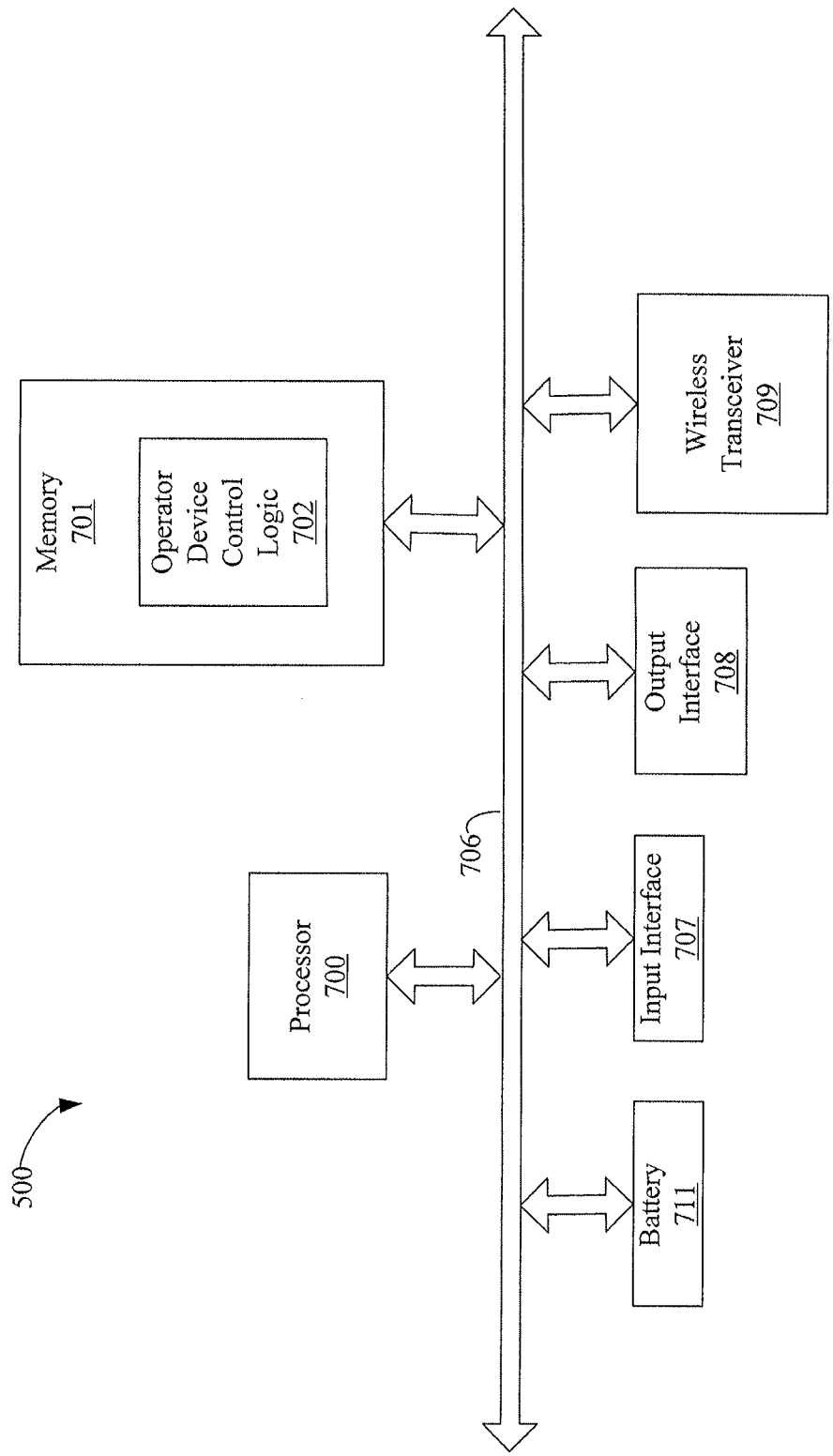
FIG. 5 is a block diagram of an exemplary operator device of the decontamination system of FIG. 3.

FIG. 5 is a block diagram of an exemplary operator device 500 in accordance with an embodiment of the present disclosure. The exemplary operator device 500 generally comprises processor 700, output interface 708, input interface 707, a wireless transceiver 709, and a communication interface 710. Each of these components communicates over local interface 706, which can include one or more buses.

The operator device 500 further comprises operator device control logic 702. Operator device control logic 702 can be software, hardware, or a combination thereof. In the exemplary operator device 500 shown in FIG. 5, operator device control logic 702 is software stored in memory 701. Memory 701 may be of any type of memory known in the art, including, but not limited to random access memory (RAM), read-only memory (ROM), flash memory, and the like.

As noted hereinabove, operator device control logic 702 is shown as stored in memory 701. When stored in memory 701, operator device control logic 702 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium Processor 700 may be a digital processor or other type of circuitry configured to run the operator device control logic 702 by processing and executing the instructions of the operator device control logic 702. Further, the processor 700 communicates with and drives the other elements within the operator device 500 via the local interface 706.

The wireless transceiver 709 may be, for example, a low-powered radio device, e.g., a radio semiconductor, radio frequency antenna (RF antenna) or other type of communication device, which communicatively couples the operator device 500 with the other system components. In this embodiment, the wireless transceiver 709 is a wireless transceiver that is configured to wirelessly transmit data to and wirelessly receive messages from the system components.

The output interface 708 is any type of device for providing information to the operator 502 (FIG. 3). In this regard, the output interface may be, for example, a touchscreen display device. Other types of output interfaces 708 may be, for example, an audio device that provides instructions to the operator audibly, light emitting diodes (LED) that show status of the system 100, or any other type of output interface that provides sensory information to the operator. While some examples have been given, other types of output interfaces may be used in other embodiments of the present disclosure The input interface 707 is any device that enables the operator to input data into the operator device 500. In one embodiment, the input interface 607 is a touchscreen that allows the user to provide information to the operator device 500 by selecting areas on the touch screen. In another embodiment, the input interface 707 may be, for example, a keyboard or a microphone. In this regard, the operator may use the keyboard to type data into the operator device 500. While some examples have been given, other types of input interfaces may be used in other embodiments of the present disclosure.

In addition, the operator device 500 comprises a battery 711. The battery 711 supplies power to the operator device 500.

During operation, the operator 502 (FIG. 3) uses the operator device 500 to indirectly control the decontamination system 100 via communication with the central computing device 504. As will be described further herein, the operator 502 may enter data indicative of parameters of the decontamination process and transmit the data to the central computing device 504. Upon receipt, the central computing device control logic 602 (FIG. 4) translates the data received into instructions for operating the system 100.

As an example, when the driver (not shown) of the vehicle 101 (FIG. 2) exits the shelter 105, then decontamination can begin. In such an example, after the operator 502 ensures that the driver is clear of the shelter 105, the operator 502 enters input into the operator device 500 to begin the decontamination process. The operator device 500 transmits data indicative of the input to the central computing device 504. In response, the central computing device control logic 602 (FIG. 3) begins the process of decontamination, i.e., activating the fluid delivery system 507 (FIG. 3) and the track and gantry system 200 (FIG. 3).

Figure 10:
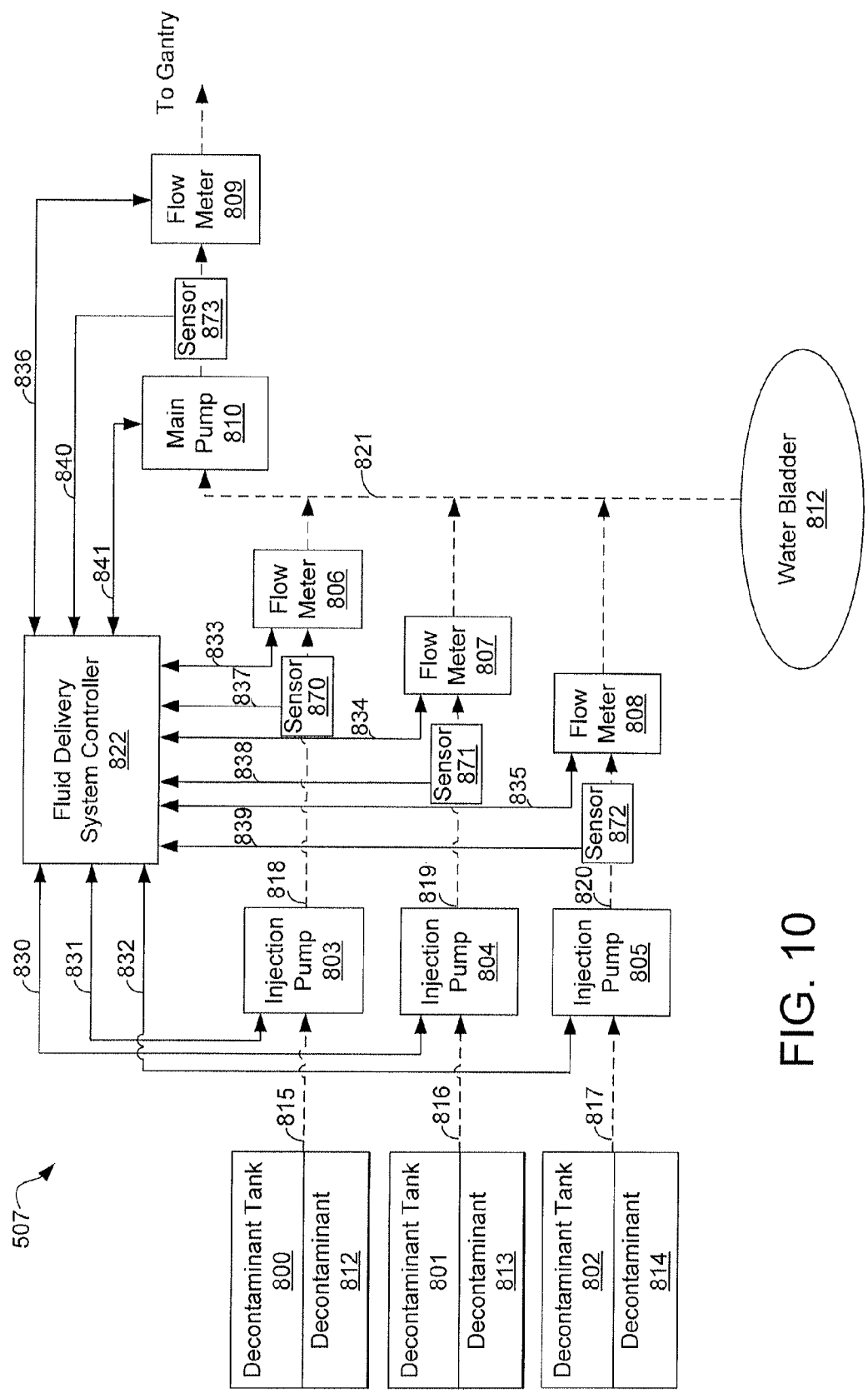
FIG. 10 is an exemplary fluid delivery system of the decontamination system such as is depicted in FIG. 3.

As another example, which is described further herein with reference to FIG. 10, the operator 502 may enter data indicative of concentrations of particular decontaminants for delivery to the gantry 300, which the operator device 500 transmits to the central computing device 504. During the decontamination process, the central computing device control logic 602 may control a pump speed associated with the particular decontaminant to ensure delivery of the specified concentration of the decontaminant.

Figure 6:
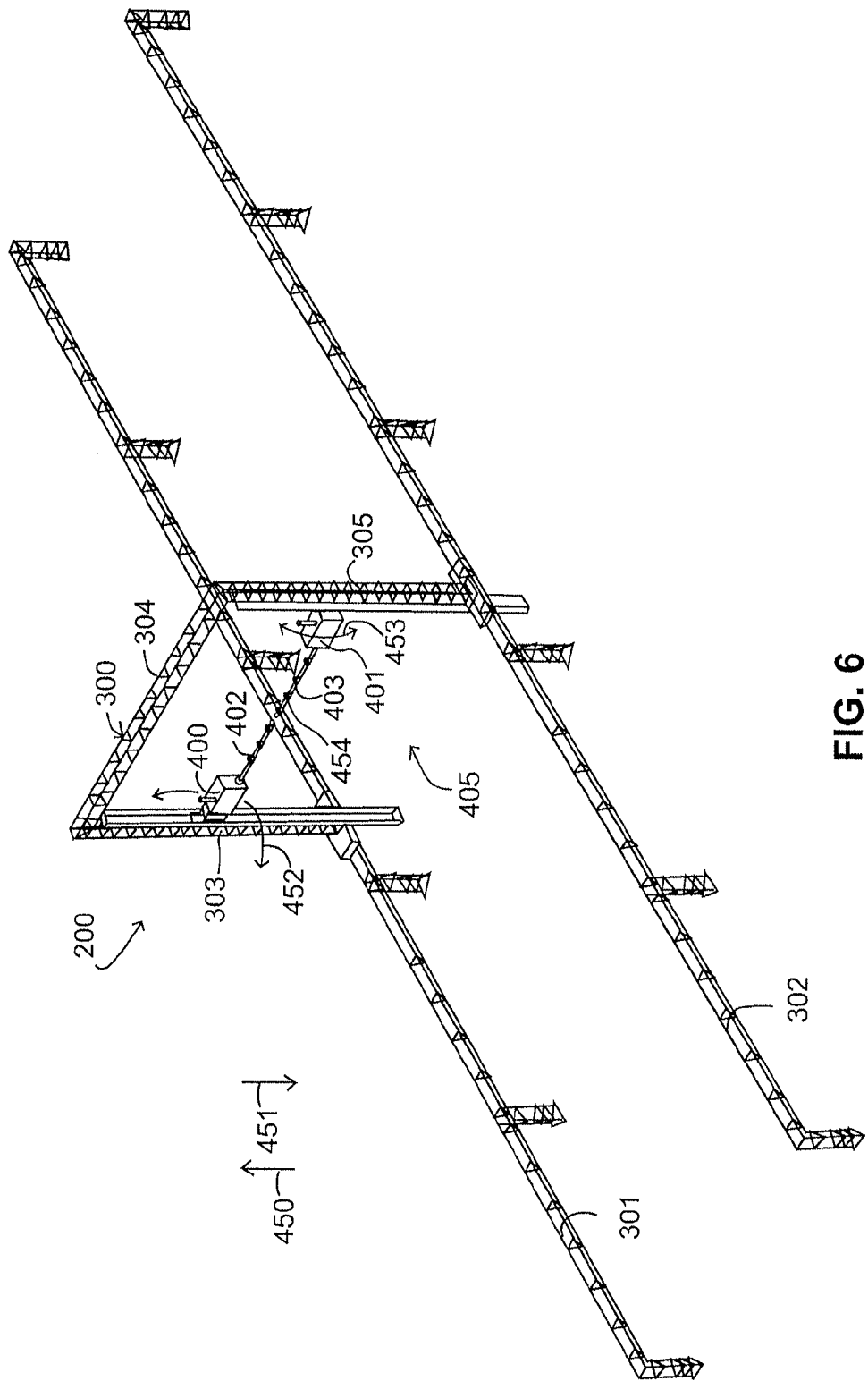
FIG. 6 is a perspective view of an exemplary track and gantry system such as is depicted in FIG. 2 with the vehicle removed.

FIG. 6 depicts the track and gantry system 200 with the vehicle 101 (FIG. 2) removed for clarity and completeness of discussion. Note that in the depiction of FIG. 6, the spray arms 402 and 403 are actuated such that they meet at a center point and are perpendicular to the tracks 301 and 302, respectively.

As discussed above with reference to FIG. 2, the track and gantry system 200 comprises the parallel tracks 301 and 302 and the U-shaped gantry 300. In addition, the track and gantry system 200 further comprises the control boxes 400 and 401. The control boxes 400 and 401 are rotationally coupled to the legs 303 and 305, respectively, of the gantry 300. Further, the spray arms 402 and 403 are rotationally coupled to the control boxes 400 and 401, respectively.

During operation, the control boxes 400 and 401 are adapted to move upward and downward in directions indicated by reference arrows 450 and 451, respectively. Further, the control boxes 400 and 401 are adapted to rotate in directions indicated by reference arrows 452 and 453, respectively, relative to the legs 303 and 306, respectively. Additionally, the spray arms 402 and 403 are adapted to rotate relative to the control boxes 400 and 401, which are described further with reference to FIG. 7.

Figure 7:
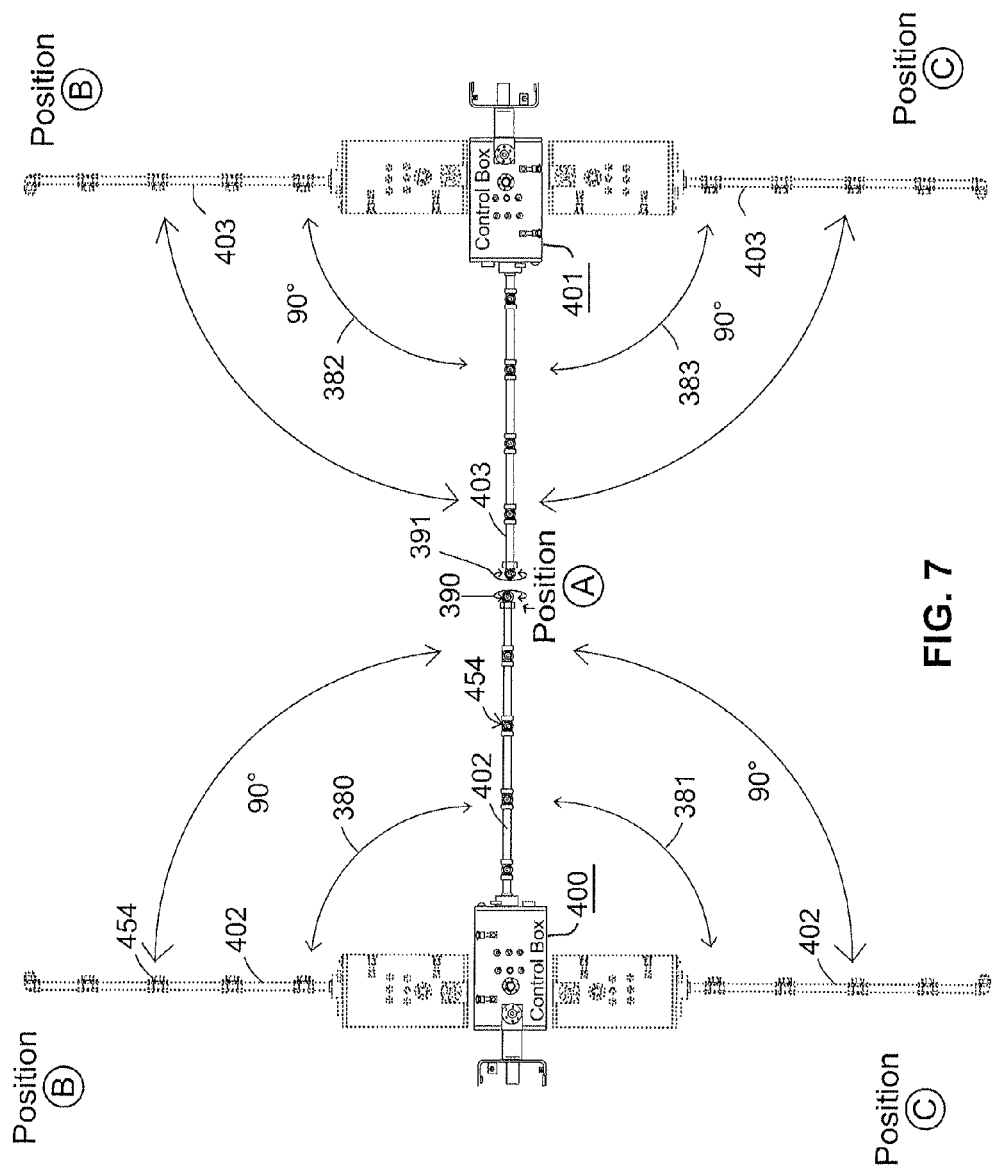
FIG. 7 is a top view of exemplary control boxes and exemplary spray arms of the track and gantry system such as is depicted in FIG. 6.

FIG. 7 is top view of the control boxes 400 and 401 and their respective rotationally coupled spray arms 402 and 403. The spray arms 402 and 403 are shown meeting at a center point and perpendicular to the tracks 301 (FIG. 6) and 302 (FIG. 6) at a position indicated as Position A. In Position A, the length of each spray arm 402 and 403 is such that each reaches approximately half the distance between the tracks 301 and 302.

In Position A nozzles 454 can be oriented in a direction such that decontaminants and water from the nozzles 454 are directed toward a front of the vehicle 101 (FIG. 2). Also, as indicated with reference to FIG. 6, the control boxes 400 and 401 move upward and downward in the direction indicated by the reference arrows 450 (FIG. 6) and 451 (FIG. 6). Thus decontaminants and water can be sprayed via the nozzles 454 onto the entire front surface of the vehicle 101 when the nozzles are oriented as shown, and the control boxes 400 and 401 move upward and downward as indicated by the reference arrows 450 and 451.

In addition to the upward, downward and rotational movement of the control boxes 400 and 401, the spray arms 402 and 403 also rotate relative to the control boxes 400 and 401, respectively. In this regard, the spray arms 402 and 403 can bi-directionally rotate relative to the control boxes 400 and 401 as indicated by reference arrows 390 and 391, respectively.

Therefore, in addition to Position A, the spray arms 402 and 403 are adapted to rotate to Position B. To move to Position B, the control box 400 rotates relative to the gantry leg 303 (FIG. 6), and the spray arm 402 rotates relative to the control box 400. When the control box 400 rotates ninety degrees (90°) relative to the gantry leg 303 as indicated by reference arrow 380, and the spray arm 402 rotates one hundred and eighty degrees (180°) relative to the control box 400 as indicated by reference arrow 390, the spray arm 402 rests in Position B with the nozzles 454 pointing toward the side of the vehicle 101. Similarly, when the control box 401 rotates ninety degrees (90°) relative to the gantry leg 305 (FIG. 6) as indicated by reference arrow 382, and the spray arm 403 rotates one hundred and eighty degrees (180°) relative to the control box 401 as indicated by reference arrow 391, the spray arm 403 rests in Position B with the nozzles 454 pointing toward the other side of the vehicle 101.

Note that in Position B, the nozzles 454 are oriented in a direction such that decontaminants and water from the nozzles 454 are directed toward the side surfaces of the vehicle 101. Also, the control boxes 400 and 401 move upward and downward in the directions indicated by the reference arrows 450 and 451. Thus, decontaminants and water can be sprayed via the nozzles 454 onto the entire side surfaces of the vehicle 101.

In addition to Positions A and B, the spray arms 402 and 403 may also rotate to Position C. When the control box 400 rotates ninety degrees (90°) relative to the gantry leg 303 as indicated by reference arrow 381, the spray arm 402 rests in Position C with the nozzles 454 pointing toward the side surface of the vehicle 101. Note that because of the initial orientation of the spray nozzles 454, no additional rotation of the spray arm 402 is necessary to effectuate Position C. Similarly, when the control box 401 rotates ninety degrees (90°) relative to the gantry leg 305 as indicated by reference arrow 382, the spray arm 403 rests in Position C with the nozzles 454 pointing toward the side surface of the vehicle 101. Note that because of the initial orientation of the spray nozzles 454, no additional rotation of the spray arm 403 is necessary to effectuate Position C.

Further note that in Position C, the nozzles 454 are oriented in a direction such that decontaminants and water from the nozzles 454 are directed toward the side surfaces of the vehicle 101. Also, the control boxes 400 and 401 move in the direction indicated by the reference arrows 450 and 451. Thus decontaminants and water can be sprayed via the nozzles 454 onto the entire side surfaces of the vehicle 101.

In regard to the back end of the vehicle 101, the spray arms 402 and 403 are positioned, similar to Position A, i.e., perpendicular to the tracks 301 and 302. However, the spray arms 402 and 403 are rotated such that the nozzles 454 are pointing in the direction toward the back of the vehicle 101. When the nozzles 454 are oriented toward the back end of the vehicle, and the control boxes 400 and 401 are moved along legs 303 and 305 in the direction indicated by reference arrows 450 and 451, the entire back surface of the vehicle is sprayed with decontaminants and/or water.

Additionally, the spray arms 402 and 403 may be positioned and moved in order to decontaminate an underside of the vehicle 101. To decontaminate the underside of the vehicle 101, the control boxes 400 and 401 are moved to the bottom of the legs 301 and 302 in the direction indicated by reference arrow 451.

From Position A, the spray arms 402 and 403 are rotated ninety degrees (90°) such that the nozzles 454 point upward toward the underside of the vehicle 101. The gantry 300 then moves toward the front of the vehicle 101, as indicated by reference arrow 221 (FIG. 2) spraying the underside of the vehicle.

As indicated hereinabove, prior to spraying the vehicle 101, the central computing device computing logic 602 (FIG. 3) generates spray plan data 620 that comprises instructions for moving the control boxes 400 and 401 and the spray arms 402 and 403. In the spray plan data 620 are instructions that move the control boxes 400 and 401 such that the obstacles along the underside of the vehicle 101 are avoided when the underside is being sprayed. In this regard, when obstacles, e.g., tires, are in the path of the spray arms 402 and 403, the central computing device control logic 602 transmits instructions that rotate the control boxes 400 and 401 thereby allowing the spray arms 402 and 403 avoid the obstacles. The central computing device control logic 602 then transmits instruction that move the spray arms 402 and 403 back to their positions perpendicular to the tracks 301 and 302 to continue spraying the underside of the vehicle 101.

With further reference to FIG. 6, the spray arms 402 and 403 may be positioned both via rotation of the control boxes 400 and 401 relative to the gantry legs 303 and 305 and rotation of the spray arms 402 and 403 relative to the control boxes 400 and 401. Thus, the front, back, side, and under surfaces of the vehicle 101 may be sprayed with decontaminants and water as needed.

An exemplary spray procedure is now described with reference to FIGS. 6 and 7. To begin the spray procedure, the gantry 300 is located at one end of the vehicle 101 (FIG. 2). The spray arms are positioned perpendicular to the tracks 301 and 302 at ground level. When in this position, the spray arms 402 and 403 meet in the middle between the tracks 301 and 302 to ensure full width coverage, and the nozzles 454 are directed toward the vehicle.

The computing device control logic 602 transits an instruction to the control boxes 400 and 401 to move upward to spray the front bumper (not shown) and grill (not shown) of the vehicle 101. Once the front bumper and grill are sprayed, the central computing device control logic 602 sends an instruction to the control boxes 400 and 401 to rotate the spray arms 402 and 403, respectively, so that the nozzles 454 are pointing toward the hood, windshield, top and back of the vehicle 101, as the gantry 300 moves along the tracks 301 and 302.

Once the back of the vehicle 101 is sprayed, the gantry 300 is positioned at the rear of the vehicle 101. The central computing device control logic 602 then sends instructions to the control boxes 400 and 401 to rotate so that the spray arms 402 and 403 are parallel to the tracks 301 and 302, and to rotate the spray arms 402 and 403 so that the nozzles 454 point toward the side surfaces of the vehicle 101. As the gantry 300 moves along the length of the tracks 301 and 302, the control boxes 400 and 401 move up and down in directions indicated by reference arrows 450 and 451. Accordingly, the spray arms 402 and 403 move up and down in a synchronized fashion to ensure full coverage of the sides of the vehicle 101.

A final pass of the gantry 300 covers the underside of the vehicle 101. Because the profile data 603 (FIG. 3) is used by the central computing device control logic 602 to develop the spray plan data 620, the spray plan data 620 comprises instructions for avoiding obstacles on the underside of the vehicle, e.g., spare tire racks, wheels, and side skirts. In this regard, the spray plan data 620 is used to position the spray arms 402 and 403 so that as the gantry 300 moves along the tracks 301 and 302, the spray arms 402 and 403 do not impact the obstacles.

Figure 8:
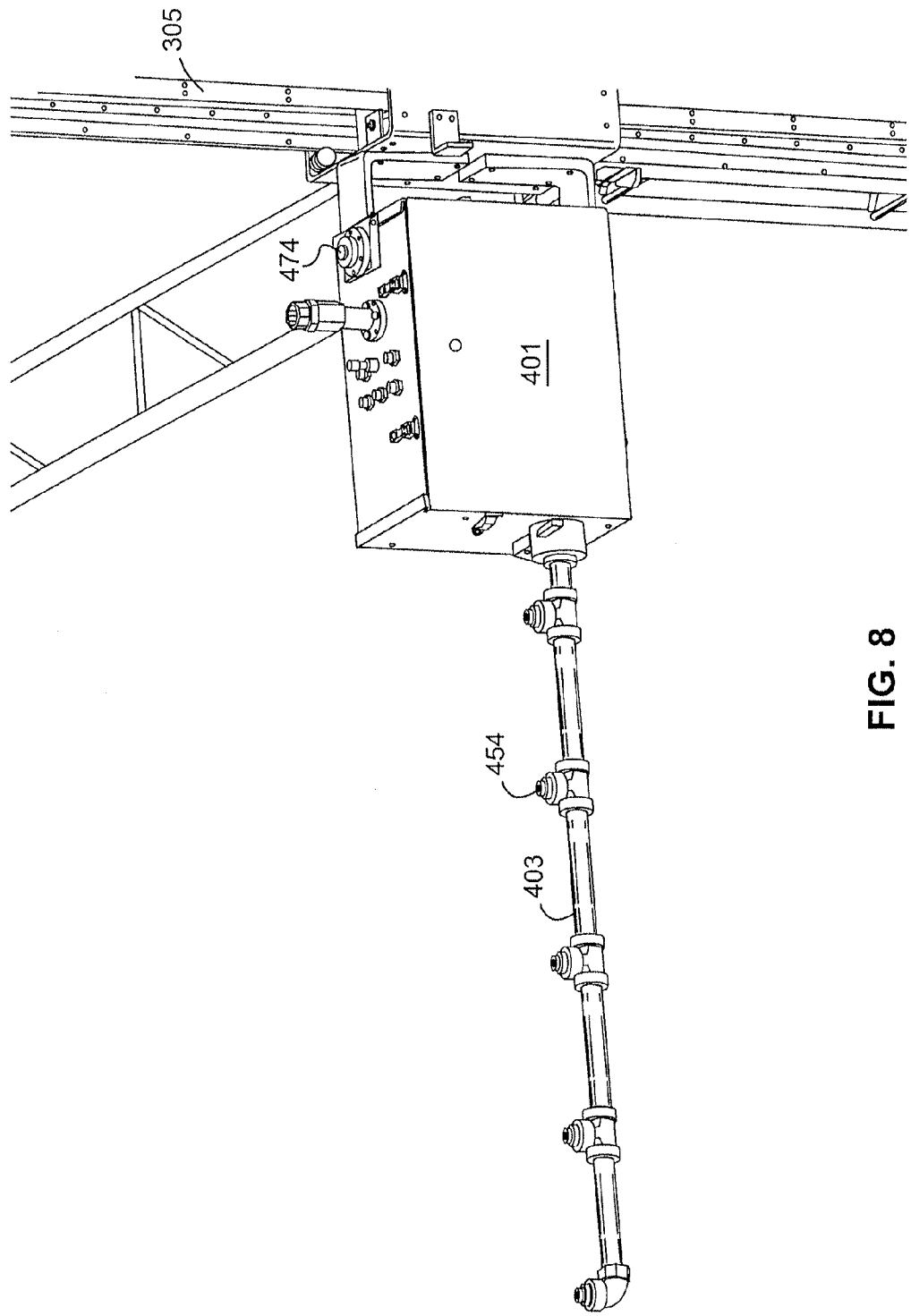
FIG. 8 is a perspective view of a control box and a spray arm such as is depicted in FIG. 7.

FIG. 8 depicts the control box 401 coupled to the spray arm 403. Note that control box 401 is substantially identical to the control box 400. For simplicity, only a detailed description of the control box 401 is now provided. However, the description equally applies to control box 400.

The control box 401 is rotationally coupled to the gantry leg 305 via a rotating joint 474. Further, the spray arm 403 is rotationally coupled to the control box 401, and comprises the plurality of nozzles 454.

Figure 9:
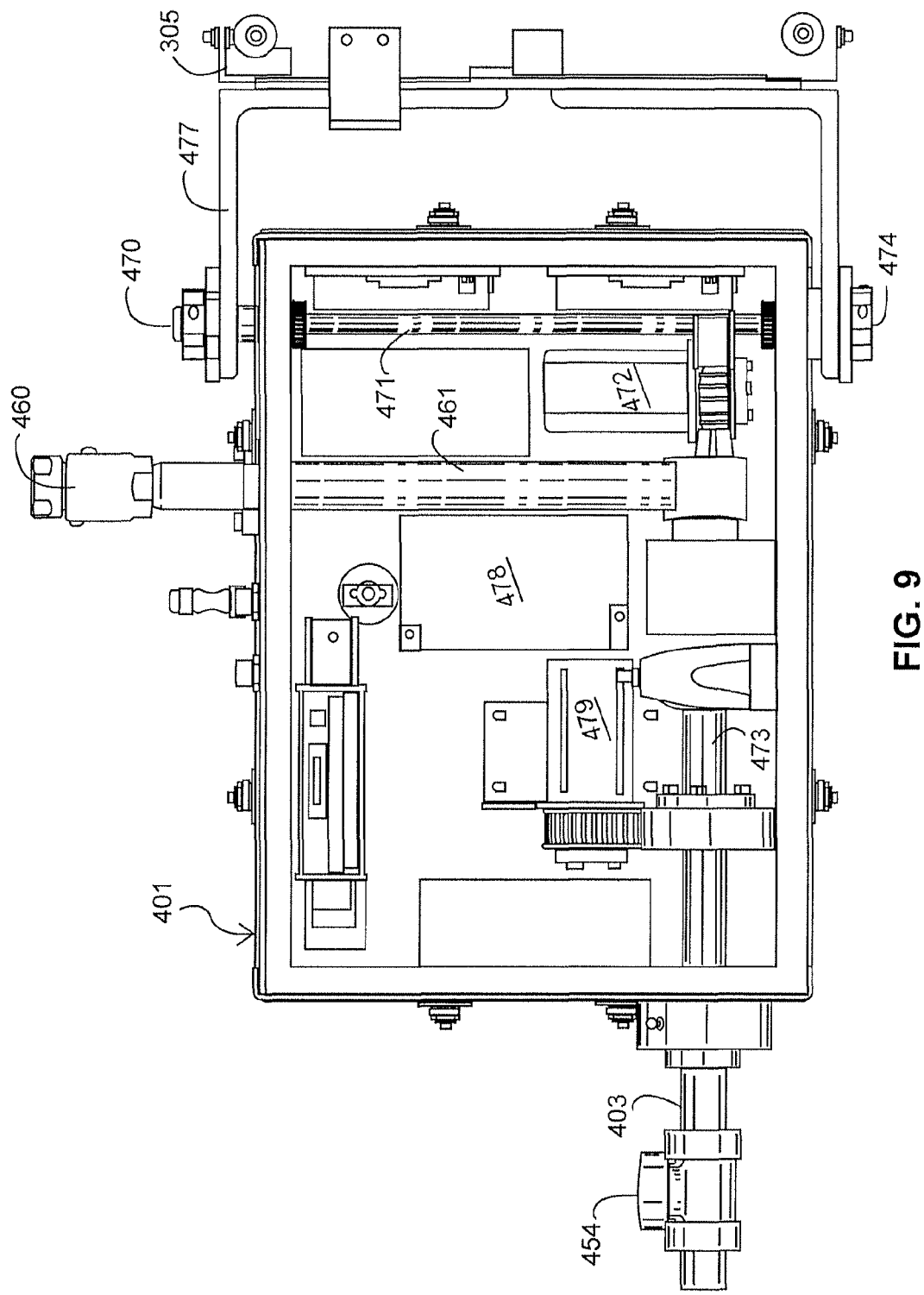
FIG. 9 is an exemplary control box such as is depicted in FIG. 8.

FIG. 9 is a cut-away view of the control box 401. In this regard, the control box 401 comprises a shaft 471 and corresponding rotating joints 474 and 479 that rotationally couple the control box 401 to a bracket 477, which is coupled to the gantry leg 305.

The control box 401 comprises a motor 472 that actuates the shaft 471 so that the control box 401 rotates relative to the gantry leg 305 in the direction indicated by the reference arrows 382 (FIG. 7) and 383 (FIG. 7). Additionally, the control box 401 comprises a motor 479 that interfaces with a shaft 473 and rotates the spray arm 403 relative to the control box 401 and in a direction indicated by reference arrow 391 (FIG. 7).

The control box 401 further comprises a fluid delivery system controller 478. The fluid delivery system controller 478 is communicatively coupled to the central computing device 504. Thus, the fluid delivery system controller 478 receives data indicative of instructions and/or commands relating to the operation of the control box 401 from the central computing device 504.

As an example, the controller 478 may receive data indicative of a command to rotate the control box 401 ninety degrees (90°) from the central computing device control logic 602. In response to the command, the fluid delivery system controller 478 transmits a signal to the motor 472 to activate and rotate the shaft 471 ninety (90°). Similarly, the fluid delivery system controller 478 may receive data indicative of a command to rotate the spray arm 403 ninety degrees (90°) from the central computing device control logic 602. In response to the command, the controller 478 transmits a signal to the motor 479 to activate and rotate the pipe 473.

Additionally, the control box 401 comprises a hose connector 460 that is coupled to a pipe 461. The hose connector 460 couples to a main conduit, which is described further herein. The main conduit delivers decontaminants and/or water to the spray arm 403. The fluid received is then sprayed through nozzles 454 onto the vehicle 101. Note that in one embodiment, the fluid received is a mixture of pre-selected concentrations of different decontaminants. For example, the fluid may be 25% of decontaminant 1, 25% of decontaminant 2, and 50% of decontaminant 3. The control of the different concentrations of fluids delivered to the vehicle 101 is described further herein.

FIG. 10 depicts an exemplary fluid delivery system 507 in accordance with an embodiment of the present disclosure. The fluid delivery system 507 comprises a fluid delivery system controller 822 that is communicatively coupled to the central computing device 504 (FIG. 3). The fluid delivery system 507 receives instructions from the central computing device 504, and the fluid delivery system controller 822 controls the components of the fluid delivery system 507 based upon the instructions received.

The exemplary fluid delivery system 507 comprises three tanks 800-802 that store decontaminants 812-814, respectively. The decontaminants can be any type of disinfectant for decontaminating the vehicle 101 (FIG. 2). As an example, the decontaminants 812-814 may be Hydrogen Peroxide ($H_2O_2$) and/or Sodium Hypochlorite (NaClO). The type of decontaminant used may be dictated by the type of disease or threat related to the vehicle 101 that is being disinfected.

The exemplary fluid delivery system 507 comprises injection pumps 803-805. Each injection pump 803-805 is in fluid communication with respective decontaminant tanks 800-802 via conduits 815-817, respectively. In this regard, pump 803 pumps decontaminant 812 from the tank 800, through conduit 815, and into a conduit 818, pump 804 pumps decontaminant 813 from the tank 801, through conduit 816, and into a conduit 819, and pump 805 pumps decontaminant 814 from the tank 802, through conduit 817, and into a conduit 820.

Each conduit 818-820 interfaces with a respective flow meter 806-808. In this regard, the flow meter 806 measures the flow rate of decontaminant 812 through the conduit 818, the flow meter 807 measures the flow rate of decontaminant 813 through the conduit 819, and the flow meter 808 measures the flow rate of decontaminant 814 through the conduit 820.

The decontaminants are delivered, via the conduits 818-820 to a main conduit 821. Thus, the fluid in main conduit 821 contains a mixture, i.e., a combination fluid, of decontaminant 812, decontaminant 813, and decontaminant 814.

The fluid delivery system 507 further comprises a main pressure pump 810 that pumps the combination fluid from the main conduit 821 to the gantry 300 (FIG. 2). The main conduit 821 interfaces with a flow meter 809 that measures the overall flow rate of the combination fluid that travels through the main conduit 821. Note that the combination fluid is delivered to the pipe 461 (FIG. 9) via the hose connector 460 (FIG. 9), and the combination fluid is delivered to the nozzles 454 (FIG. 9) via the pipe 473 (FIG. 9) for spraying the vehicle.

In one embodiment, the fluid delivery system 507 comprises one or more sensors 870-873. The sensors 870-873 are any type of devices for measuring other characteristics of the fluid through the conduits 818-821. As an example, the sensors 870-873 may be temperature sensors for measuring a temperature of the fluid flowing through the conduits 818-821. As another example, the sensors 870-873 may be pressure sensors for measuring a pressure of the fluid flowing through the conduits 818-821. Note that only a single sensor 870-873 is shown on respective conduits 818-821; however, in one embodiment, each sensor 870-873 is representative of a plurality of sensors. In this regard, multiple sensors may be used per conduit 818-821 to collect data regarding the decontaminant 812-814 flowing through conduits 818-820 or the combined fluid flowing through conduit 821.

The fluid delivery system controller 822 is communicatively coupled to each injection pump 803-805 via communication links 830-832 and to each of the flow meters 806-809 via communication links 833-836. Additionally, the fluid delivery system controller 822 is communicatively coupled to the main pump 810 via a communication link 841. The fluid delivery system controller 822 is also communicatively coupled to sensors 870-873 via communication links 837-840.

In one embodiment, the communication links 830-832 are physical cables that couple the fluid delivery system controller 822 to respective pumps 803-805. In another embodiment, the fluid delivery system controller 822 comprises a wireless transceiver (shown in FIG. 8B) that communicates with wireless transceivers (not shown) in the injection pumps 803-805.

Figure 11:
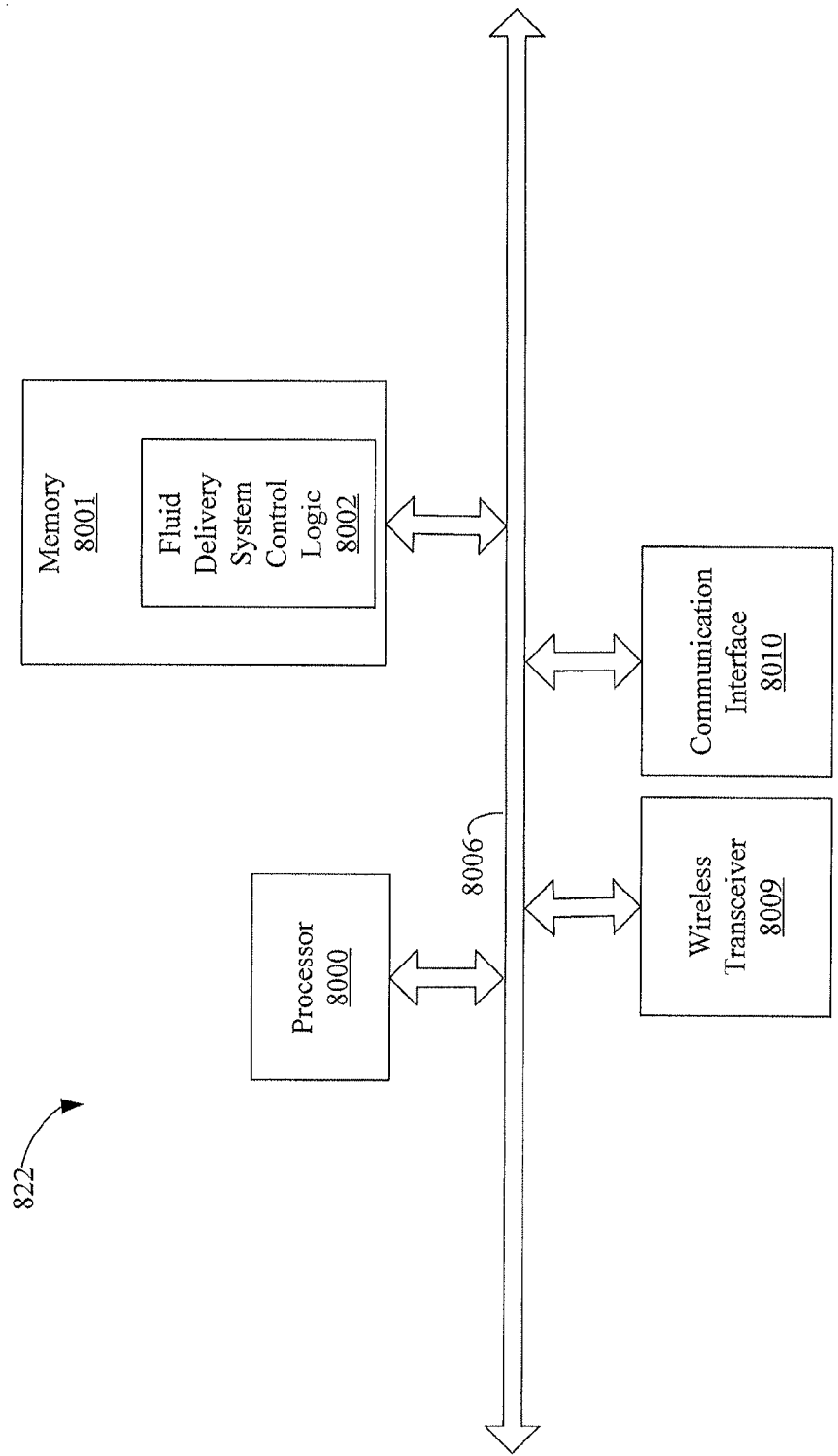
FIG. 11 is a block diagram of an exemplary fluid delivery system controller of the fluid delivery system depicted in FIG. 10.

FIG. 11 is a block diagram depicting an exemplary fluid delivery system controller 822 in accordance with an embodiment of the present disclosure. The fluid delivery system controller comprises a processor 8000, a communication interface 8010, and memory 8001. Each of these components communicates over local interface 8006, which can include one or more buses.

The fluid delivery system controller 822 further comprises fluid delivery system control logic 8002. The fluid delivery system control logic 8002 can be software, hardware, firmware, or any combination thereof. In the exemplary fluid delivery system controller 822 shown in FIG. 11, fluid delivery system control logic 8002 is software stored in memory 8001. Memory 8001 may be of any type of memory known in the art, including, but not limited to random access memory (RAM), read-only memory (ROM), flash memory, and the like.

As noted hereinabove, fluid delivery system control logic 8002 is shown as stored in memory 8001. When stored in memory 8001, fluid delivery system control logic 8002 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium Processor 8000 may be a digital processor or other type of circuitry configured to run the fluid delivery system control logic 8002 by processing and executing the instructions of the fluid delivery system control logic 8002. Further, the processor 8000 communicates with and drives the other elements within the fluid delivery system controller 822 via the local interface 8006.

In an exemplary embodiment, the communication interface 8010 is any type of communication interface that the fluid delivery system controller 822 may use to communicate with the fluid delivery system components, including the pumps 803-805 (FIG. 10), the flow meters 806-809 (FIG. 10) and/or the sensors 870-873 (FIG. 10), or the central computing device 504 (FIG. 3). For example, the communication interface 8010 may be an Ethernet interface that physically communicatively couples the fluid delivery system controller 822 to the fluid delivery system components or the central computing device 504.

In another embodiment, the fluid delivery system controller 822 comprises a wireless transceiver 8009. The wireless transceiver 8009 may be, for example, a low-powered radio device, e.g., a radio semiconductor, radio frequency antenna (RF antenna) or other type of communication device, which communicatively couples the fluid delivery system controller 822 with the other fluid delivery system components or the central computing device 504. In this embodiment, the transceiver 8009 is a wireless transceiver that is configured to transmit and receive messages wirelessly from the fluid delivery components and/or the central computing device 504.

During operation, the central computing device 504 and the fluid delivery system controller 822 bi-directionally communicate in real time during the decontamination process. In this regard, the central computing device 504 transmits data to the fluid delivery system controller 822 indicative of desired pump speeds. Additionally, the fluid delivery system controller 822 transmits data indicative of flow rates, temperature, pressure, and actual pump speeds to the central computing device 504.

Initially, the central computing device control logic 602 calculates a desired speed of each injection pump 803-805 (FIG. 10) based upon data indicative of concentrations for each decontaminant, which is received from the operator device 500 (FIG. 3). Once speeds are calculated for each of the injection pumps 803-805, the central computing device control logic 602 (FIG. 4) transmits data indicative of the speeds to the fluid delivery system controller 822. Upon receipt, the fluid delivery system control logic 8002 transmits data to each of the injection pumps 803-805 and the main pump 810 indicative of the speed at which the pumps 803-805 and 810 are to operate in order to ensure the concentrations identified by the operator flow through the main conduit 821.

While decontaminants are being delivered to the gantry 300 (FIG. 2), the central computing device control logic 602 continues to monitor and control the fluid delivery system 507 (FIG. 10). In this regard, the computing device control logic 602 continues to monitor in real-time flow rate in conduits 818-820, overall flow rate in channel 821, temperature and pressure in conduits from 818-821, and actual speed of the injection pumps 803-806. Thus, the fluid delivery system control logic 8002 obtains such data from the injection pumps 803-805, flow meters 806-809, and sensors 870-873 and transmits data indicative of these monitored parameters to the central computing device 504.

Upon receipt of data indicative of flow rates, temperature, pressure, and actual speeds, the central computing device control logic 602 calculates the discrete error between the desired concentration (as indicated by the operator) and the actual concentration measured by the flow meters 806-809. The central computing device control logic 602 performs a proportional-integral-derivative (PID) control loop with specially tuned gains and control coefficients to calculate the speeds for the injection pumps 806-808 and the main pump 810 to meet the desired concentrations. In this regard, the central computing device control logic 602 calculates the desired speeds for the pumps 806-809 and transmits data indicative of the desired speeds to the fluid delivery system controller 822 every few seconds. In response, the fluid delivery system control logic 8002 transmits data indicative of the desired speeds to each of the respective pumps 803-805 and 810.

Figure 12:
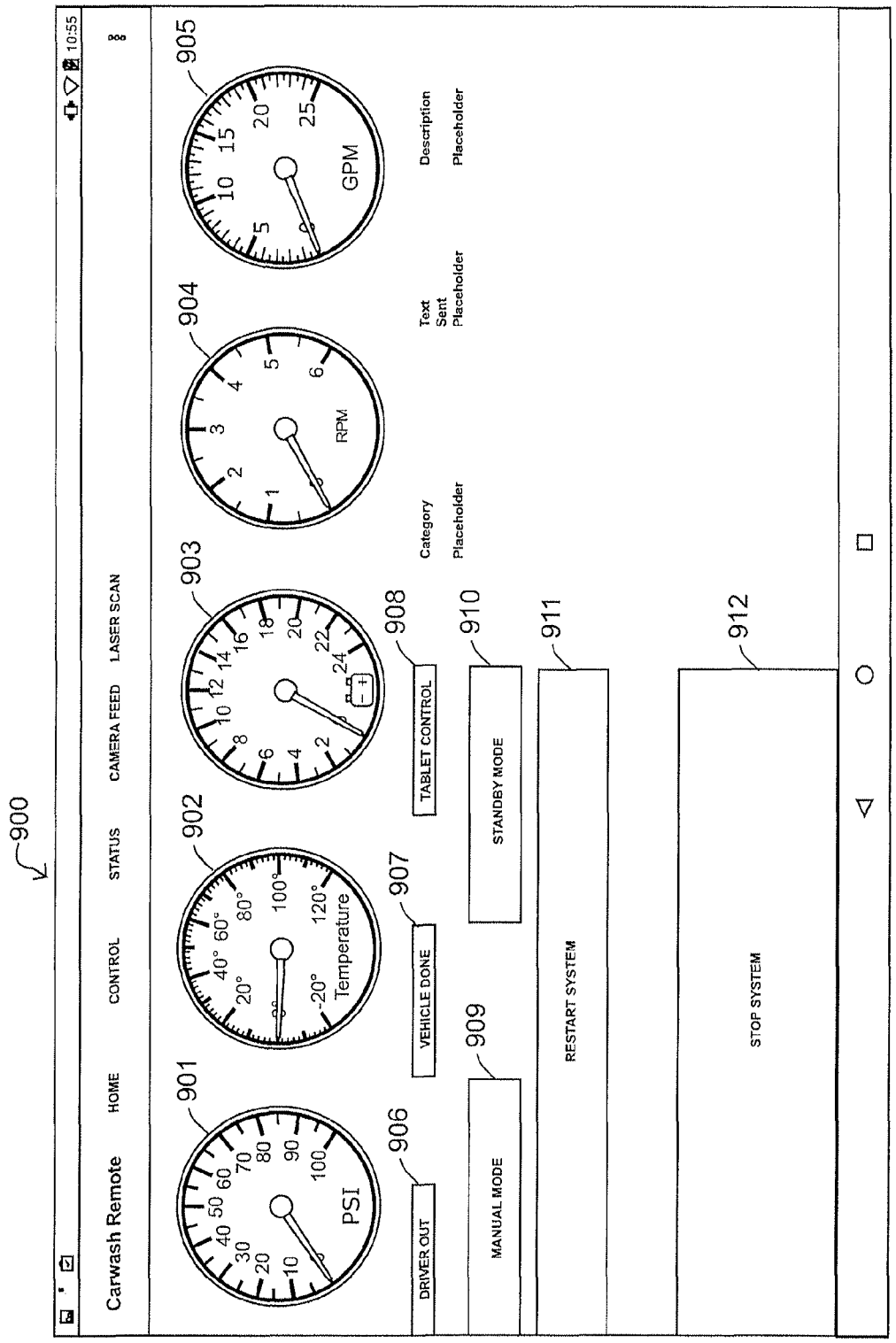
FIG. 12 is an exemplary "HOME" graphical user interface (GUI) of the decontamination system such as is depicted in FIG. 3.

FIG. 12 is an exemplary "Home" graphical user interface (GUI) 900 that is displayed by the operator device control logic 702 (FIG. 5) to an operator via the output interface 708 (FIG. 5) of the operator device 500 (FIGS. 3 and 5). During decontamination, the central computing device 504 receives data from the fluid delivery system 507 (FIG. 3) related to the main conduit 821 and main pump 810. In response, the central computing device control logic 602 (FIG. 4) transmits data indicative of the information related to the main conduit to the operator device 500. Upon receipt, the operator device control logic 702 displays the GUI 900 comprising information indicative of the data received from the central computing device 504 to the output interface 708.

The Home GUI 900 comprises graphical gauges 901-905. Gauge 901 displays the pressure detected in the main conduit 821 (FIG. 10). Gauge 902 displays the temperature in the main conduit 821, and gauge 903 displays the battery power of the battery (not shown) of the operator device 500. Additionally, gauge 904 displays the revolutions per minute of the main pump 810, and gauge 905 displays the gallons per minute (GPM) of the main pump 810.

The Home GUI 900 further comprises a "Driver Out" pushbutton 906. When a driver (not shown) has exited the vehicle 101 (FIG. 1) and cleared the shelter 105 (FIG. 1), the operator selects pushbutton 906 to indicate that the driver is out of the vehicle 101 and cleared the shelter 105. Decontamination of the vehicle 101 begins upon selection by the operator of the "Driver Out" pushbutton 906.

The Home GUI 900 further comprises a "Vehicle Done" status identifier 907. When the decontamination process is complete, this identifier 907 alerts the operator 502 that the driver of the vehicle 101 can reenter his/her vehicle.

The Home GUI 900 further comprises a "Tablet Control" pushbutton 908. Upon start-up of the decontamination system 100, the central computing device 504 is initially in control of the system 100. This is done by default. When an operator 502 selects the "Tablet Control" pushbutton 908, the central computing device control logic 602 automatically gives control of the system 100 to the operator device 500. Thereafter, the system 100 is controlled by the operator through use of the operator device 500.

The Home GUI 900 further comprises a "Manual Mode" pushbutton 909. The "Manual Mode" pushbutton 909, when selected, places the system 100 in manual mode. In manual mode, the operator 502 can transmit specific commands to the central computing device 504 for operating the system 100. Manual mode may be used for testing, calibration, and for decontamination of uniquely-shaped equipment. As an example, the operator 502 man transmit a command to the central computing device 504 indicative of a particular movement of the gantry. In response, the central computing device control logic 602 transmits a command to the gantry indicative of the movement, and the gantry moves accordingly.

The Home GUI 900 further comprises a "Standby Mode" identifier 910. This identifier indicates that the system is in autonomous mode and ready for a vehicle to enter the tunnel.

The Home GUI 900 further comprises a "Restart System" pushbutton 911. When the operator 502 (FIG. 5) selects the "Restart System" pushbutton 911, the operator device control logic 702 transmits a message via transceiver 709 to the central computing device 504, and in response, the central computing device control logic 602 begins the decontamination process again.

The Home GUI 900 further comprises a "Stop System" pushbutton 912. When the operator 502 selects the "Stop System" pushbutton, the operator device control logic 702 transmits a message via transceiver 709 to the central computing device 504, and in response, the central computing device control logic 602 stops the decontamination process.

Figure 13:
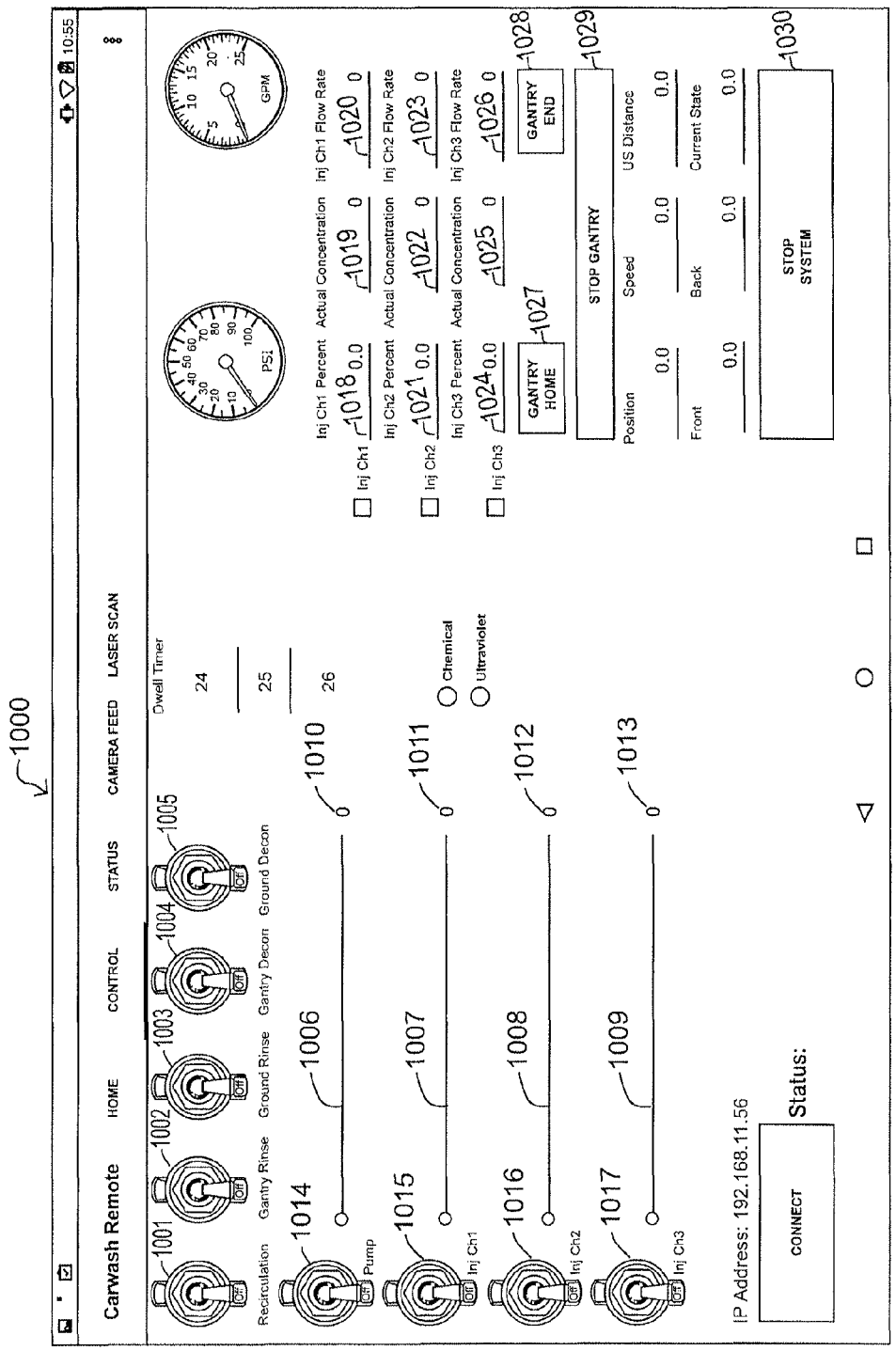
FIG. 13 is an exemplary "CONTROL" GUI of the decontamination system such as is depicted in FIG. 3.

FIG. 13 is an exemplary "Control" graphical user interface (GUI) 1000 that is displayed by the operator device control logic 702 (FIG. 7) to an operator via the output interface 708 (FIG. 7) of the operator device 500 (FIGS. 5 and 7). The Control GUI 1000 comprises controls for controlling and monitoring the system 100. Thus, an operator 502 (FIG. 5) can enter data into Control GUI 1000 for controlling the operation of the system 100, and the operator device control logic 702 transmits data indicative of the control data input to the central computing device 504. Additionally, the Control GUI 1000 displays information received from the central computing device 504.

The Control GUI 1000 comprises virtual knobs 1001-1005 that show when a particular phase of decontamination is occurring. Knob 1001 indicates when recirculation is occurring, knob 1002 indicates when the gantry is rinsing an object, knob 1003 indicates when ground rinse is occurring, knob 1004 indicates when the gantry is spraying decontaminants, and knob 1005 indicates when ground decontamination is occurring. Data indicative of the statuses of these various processes is received from the central computing device 504, and the operator device control logic 702 displays this data to the Control GUI 1000.

The Control GUI 1000 further comprises sliders 1006-1009. The sliders 1006-1009 when actuated by the operator enable the operator to select a concentration of a particular decontaminant or concentration of the combined fluid that is in main conduit 821.

In this regard, slider 1006 may be slid to the right to increase the concentration of the combined fluid found in the main conduit 821. A number 1010 to the right of the slider 1006 indicates the percentage being selected by the slider 1006. Further, there is a status knob 1014 indicating status of the main pump 810, i.e., whether the pump 810 is off or operating.

The operator 502 may slide the slider 1007 to the right to increase the concentration of the decontaminant being pumped into conduit 818 (FIG. 10) by injection pump 803 (FIG. 10). A number 1011 to the right of the slider 1007 indicates the concentration percentage being selected by the slider 1007. For example, the operator may desire that the combination fluid in conduit 821 have ten percent (10%) of the decontaminant 812. Thus, the operator 502 actuates the slider to the right until the number 1011 indicates ten percent (10%). Further, there is a status knob 1015 indicating status of the injection pump 803, i.e., whether the pump 803 is off or operating.

Slider 1008 may be slid to the right to increase the concentration of the decontaminant being pumped into conduit 819 (FIG. 10) by injection pump 804. A number 1012 to the right of the slider 1008 indicates the concentration percentage being selected by the slider 1008. For example, the operator may desire that the combination fluid in conduit 821 (FIG. 10) have thirty percent (30%) of the decontaminant 813. Thus, the operator 502 actuates the slider to the right until the number 1013 indicates thirty percent (30%). Further, there is a status knob 1016 indicating status of the injection pump 804, i.e., whether the pump 804 is off or operating.

Slider 1009 may be slid to the right to increase the concentration of the decontaminant being pumped into conduit 820 (FIG. 10) by injection pump 805. A number 1013 to the right of the slider 1009 indicates the concentration percentage being selected by the slider 1009. For example, the operator may desire that the combination fluid in conduit 821 have twenty percent (20%) of the decontaminant 814. Thus, the operator 502 actuates the slider to the right until the number 1013 indicates twenty percent (20%). Further, there is a status knob 1017 indicating status of the injection pump 805, i.e., whether the pump 805 is off or operating.

In regards to sliders 1006-1009, the operator 504 is selecting concentration of particular decontaminants for the system 100. After the data is entered, the operator device control logic 702 transmits data indicative of the concentrations to the central computing device 504. As described hereinabove, the central computing device control logic 602 uses the data to control delivery of decontaminants to the gantry via the fluid delivery system 507.

Additional information regarding a decontamination process is further displayed to the Control GUI 1000. In the exemplary GUI 1000, fields 1018-1020 display the percentage of decontaminant being delivered, the actual concentration being delivered, and the flow rate detected for conduit 818 and injection pump 803. Further, fields 1021-1023 display the percentage of decontaminant being delivered, the actual concentration being delivered, and the flow rate detected for conduit 819 and injection pump 804. Additionally, fields 1024-1026 display the percentage of decontaminant being delivered, the actual concentration being delivered, and the flow rate detected for conduit 820 and injection pump 805.

The Control GUI further comprises a "GANTRY HOME" pushbutton 1027. If selected by the operator 502, the operator device control logic 702 transmits data indicating that the user desires the gantry 300 be moved to its initial position. In response, the central computing device 504 transmits data to the track and gantry system 200 (FIG. 2) to move the gantry to its initial position. Similarly, the Control GUI further comprises a "GANTRY END" pushbutton 1028. If selected by the operator 502, the operator device control logic 702 transmits data indicating the user desires the gantry to be moved to the end of the vehicle 101.

The Control GUI 1000 further comprises a "STOP GANTRY" pushbutton 1029 that, when selected by the operator, transmits data to the central computing device 504 to stop movement of the gantry 300. In response, the central computing device transmits data indicative of stopping the gantry 300 to the track and gantry system 200.

The Control GUI 1000 further comprises a "STOP SYSTEM" pushbutton 1030 that, when selected by the operator 402, transmits data to the central computing device 504 to stop the system 100 (FIG. 1). In response, the central computing device control logic 602 transmits data indicative of stopping the system to the track and gantry system 200 and the fluid delivery system 507. Thus, the entire system 100 is halted.

Figure 14:
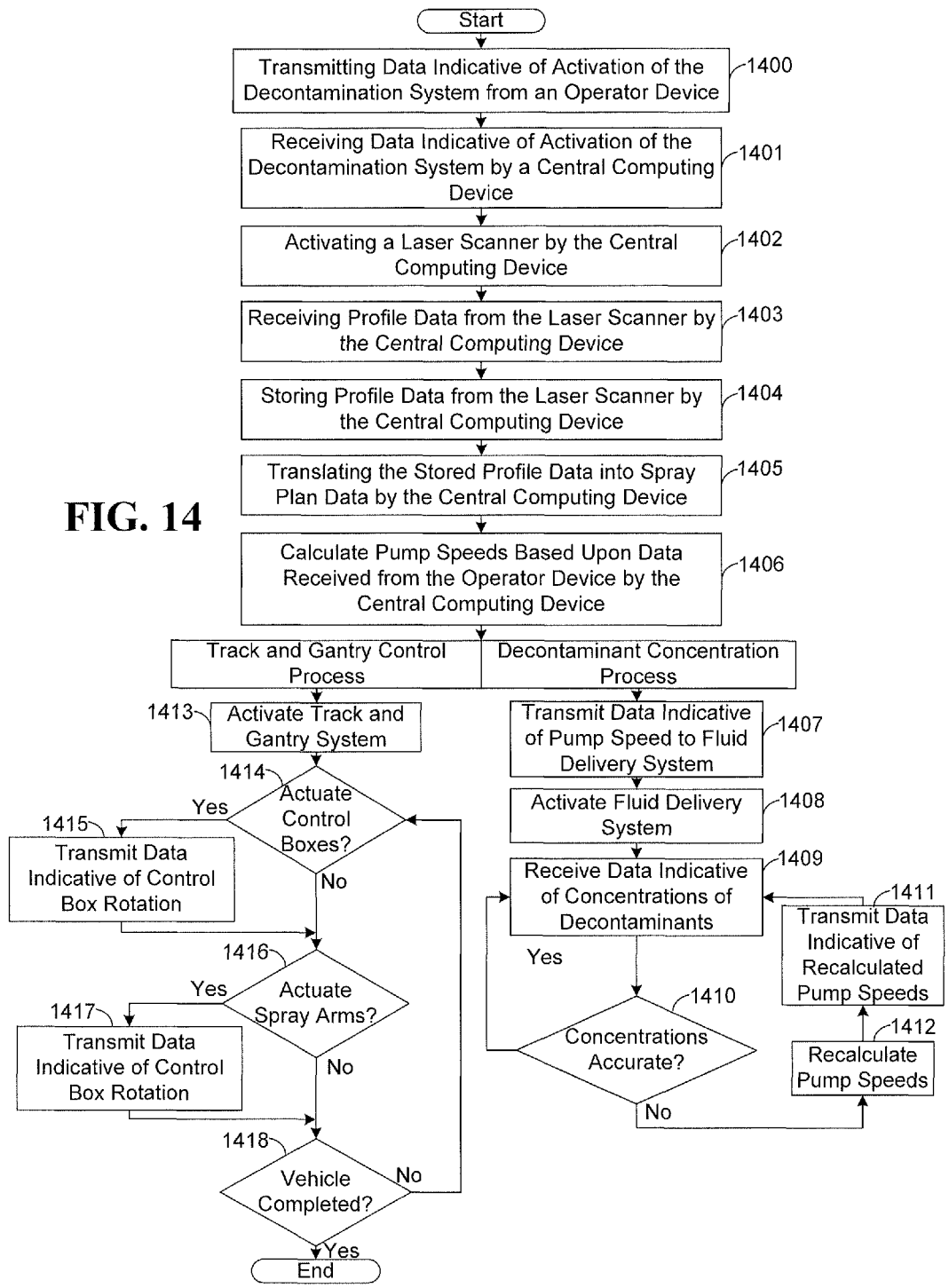
FIG. 14 is a flowchart depicting exemplary architecture and functionality of the decontamination system such as is depicted in FIG. 3.

FIG. 14 depicts a flowchart of exemplary architecture and functionality of the decontamination system 100 in accordance with an embodiment of the present disclosure. In operation, a driver (not shown) of the vehicle 101 (FIG. 2) drives the vehicle 101 into on entry opening in the shelter 105. The driver exits the vehicle 101 and the shelter 105 (FIG. 1).

Once the driver has exited the shelter 105, an operator 502 (FIG. 3) of the operator device 500 (FIGS. 3 and 5) initiates a decontamination process. In one embodiment, the operator 502 of selects the "Driver Out" pushbutton 906 (FIG. 12), and in response, the operator device control logic 702 (FIG. 5) transmits initiation data to the central computing device 504 to start the decontamination process, as indicated in step 1400. In one embodiment, the operator device 500 is a portable, hand-held device, such as, for example, an iPad, personal digital assistant (PDA), or a cellular phone. In another embodiment, the operator 502 may initiate decontamination via the input interface 607 (FIG. 4) of the central computing device 504 (FIGS. 3 and 4). Note that in one embodiment, the data transmitted to the central computing device 504 may include data indicative of selected decontaminants and a percentage concentration of the selected decontaminants to be sprayed on the vehicle 101.

In response to receiving the data indicative of initiation in step 1401, the central computing device logic 602 activates the laser scanner 364 (FIG. 2), as indicated in step 1402. Upon activation, the laser scanner 364 scans the vehicle 101 and collects data indicative of the profile of the vehicle 101. Once the scan is complete, the laser scanner 364 transmits the collected data indicative of the profile of the vehicle 101 to the central computing device 504, and the central computing device control logic 602 stores the received data as profile data 603 (FIG. 3), as indicated in step 1404.

After storing the profile data 603, the central computing device control logic 602 translates the profile data 603 into spray plan data 620 (FIG. 4), as indicated in step 1405. As described hereinabove, the laser scanner collects data indicative of x, y, and z coordinates of the profile of the vehicle 101. The central computing device control logic 602 generates a three-dimensional model of the vehicle based upon the profile data 603. Based upon the three-dimensional model, the central computing device control logic 602 generates spray plan data 620. The spray plan data 620 comprises a plurality of instructions for actuating the control boxes 400 (FIG. 6) and 401 (FIG. 6) and the spray arms 402 (FIG. 6) and 403 (FIG. 6) so that every surface on the vehicle 101 is sprayed in its entirety.

In step 1406, the central computing device control logic 602 calculates pump speeds based upon data received from the operator device 500. As described above, the operator 502 can enter data via GUI 1000 that identifies concentrations for each of the decontaminants 812-814 (FIG. 10). Based upon the identified concentrations, the central computing device logic 602 calculates pump speeds for respective pumps 803-805 (FIG. 10) for delivering the identified concentrations to the main conduit 821 (FIG. 10).

At this point in the process, the central computing device control logic 602 simultaneously performs a track and gantry control process and a decontaminant concentration process.

In the track and gantry control process, the central computing device control logic 602 activates the track and gantry system 200 in step 1413. Note that the central computing device control logic 602 controls actuation of the control boxes 400 and 401 and the spray arms 402 and 403 based upon the spray plan data 620, as described above. In this regard, if the spray plan data 620 indicates that the control boxes 400 and 401 are to be actuated at a particular time in the sequence in step 1414, the central computing device control logic 602 transmits data indicative of control box actuation, as indicated in step 1415. If the spray plan data 620 indicates that the spray arms 402 and 403 are to be actuated, as indicated in step 1416, the central computing device control logic 602 transmits data indicative of spray arm rotation, as indicated in step 1417.

When the spray plan data 620 indicates that the vehicle spray has been completed, as indicated in stop 1418, the decontamination process ends.

In the decontamination concentration process, the central computing device control logic 602 transmits data indicative of pump speed to the fluid delivery system controller 822 (FIG. 10). In response, the fluid delivery system controller 822 activates the pumps 803-804 at the speeds identified in the received data, as indicated in step 1408.

Periodically, in real time, the fluid delivery system controller 822 transmits data indicative of concentrations of the decontaminants as indicated by the flow meters 806-809. The central computing device control logic 602 receives the data indicative of the concentrations of the decontaminants, as indicated in step 1409. If the concentrations are not accurate, i.e., do not match the concentrations as provided by the operator 502 via the operator device 500 in step 1410, the central computer control logic 602 recalculates pump speed, as indicated in step 1412. After recalculation, the central computing device control logic 602 transmits data indicative of the recalculated pump speeds to the fluid delivery system controller 822, as indicated in step 1411. In response, the fluid delivery system controller 822 transmits signals to the pumps 803-805 setting the pumps to the recalculated pump speeds. This process continues throughout the decontamination process.

What is claimed is:

1. A decontamination method for decontaminating an object, comprising:
   initiating spray in a first direction through one or more nozzles of a spray arm rotationally coupled to a control box in a first position and rotationally coupled to a leg of a gantry that is moveably coupled to a track;
   rotating the control box to a second position based on profile data of the object;
   monitoring a concentration of fluid in a main pipe;
   modifying a speed of a pump based upon the concentration of the fluid in the main pipe; and
   receiving a user input indicating a desired concentration of the fluid in the main pipe.

2. The decontamination method of claim 1, further comprising rotating the spray arm so that the one or more nozzles are spraying in a second direction based on the profile data.

3. The decontamination method of claim 1, further comprising collecting, via a laser scanner, data indicative of a profile of the object when the gantry is moving relative to the track.

4. The decontamination method of claim 3, further comprising transmitting, by the laser scanner, the profile data to a central computing device.

5. The decontamination method of claim 4, further comprising:
   receiving the profile data by the central computing device; and
   storing the profile data in resident memory by the central computing device.

6. The decontamination method of claim 1, further comprising generating a spray plan corresponding to the object based upon the profile data received.

7. The decontamination method of claim 1, further comprising:
   receiving, by an operator device, a user input;
   transmitting data indicative of the user input to a central computing device;
   receiving the data indicative of the user input; and
   activating decontamination of the object based upon the user input.

8. The decontamination method of claim 1, further comprising:
   receiving data indicative of the desired concentration from an operator device; and
   modifying, by a central computing device, a speed of the pump based upon the data indicative of the desired concentration.

* * * * *